US009901725B2

(12) United States Patent
Spohn et al.

(10) Patent No.: US 9,901,725 B2
(45) Date of Patent: Feb. 27, 2018

(54) OVERMOLDED MEDICAL CONNECTOR TUBING AND METHOD

(71) Applicant: Medrad, Inc., Indianola, PA (US)

(72) Inventors: Michael A. Spohn, Butler, PA (US); Cory J. Price, Coraopolis, PA (US); Andrew W. Meier, Wexford, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 1111 days.

(21) Appl. No.: 13/632,598

(22) Filed: Oct. 1, 2012

(65) Prior Publication Data

US 2014/0091569 A1    Apr. 3, 2014

(51) Int. Cl.
*A61M 39/08* (2006.01)
*B29C 47/00* (2006.01)
(Continued)

(52) U.S. Cl.
CPC ............ *A61M 39/08* (2013.01); *A61M 39/10* (2013.01); *A61M 39/12* (2013.01);
(Continued)

(58) Field of Classification Search
CPC ................ A61M 39/08; A61M 25/005; A61M 25/0012; A61M 25/0014; A61M 39/10;
(Continued)

(56) References Cited

U.S. PATENT DOCUMENTS 1,718,474 A    6/1929  McQuaid
1,748,810 A    2/1930  Barney
(Continued)

FOREIGN PATENT DOCUMENTS

CN    1747762 A    3/2006
EP    2514478 B1   7/2013
(Continued)

OTHER PUBLICATIONS

The International Preliminary Report on Patentability from corresponding PCT Application No. PCT/US2013/061275 dated Apr. 16, 2015.

(Continued)

*Primary Examiner* — Gregory J Binda
*Assistant Examiner* — Zachary T Dragicevich
(74) *Attorney, Agent, or Firm* — Joseph L. Kent; David Schramm; James R. Stevenson (57) ABSTRACT

A high pressure medical connector tubing assembly includes a high pressure medical connector tubing assembly, including a tube element having opposed tube ends and a passageway, an end element overmolded to at least one of the opposed tube ends, the end element having an annular end portion having a preselected length, and a connector element having a connector hub defining a receiving cavity. The preselected length of the annular end portion may be used to pre-control the axial location of stress concentration in the connector hub. A method of forming the high pressure medical connector tubing assembly includes providing a tube element comprising opposed tube ends and a passageway therethrough, overmolding an end element onto at least one of the opposed tube ends, providing a connector element comprising a connector hub defining a receiving cavity, and securing the tube end with the overmolded end element in the receiving cavity.

18 Claims, 7 Drawing Sheets

(51) Int. Cl.
*B29C 47/02* (2006.01)
*B29C 47/06* (2006.01)
*A61M 39/10* (2006.01)
*A61M 39/12* (2006.01)

(52) U.S. Cl.
CPC ...... *B29C 47/0023* (2013.01); *B29C 47/0028* (2013.01); *B29C 47/0033* (2013.01); *B29C 47/021* (2013.01); *B29C 47/065* (2013.01); *A61M 2039/082* (2013.01); *B29C 2947/92514* (2013.01); *B29C 2947/92761* (2013.01)

(58) Field of Classification Search
CPC .. A61M 2039/1077; A61M 2039/1088; A61M 2039/1044; A61M 39/12; A16M 2039/082; F16L 47/02; B29C 47/065; B29C 47/0033; B29C 47/021; B29C 47/0028; B29C 47/0023; B29C 2947/92514; B29C 2947/92761
USPC ........ 285/222.1, 288.1, 293.1; 604/533, 534, 604/535, 527
See application file for complete search history.

(56) References Cited

U.S. PATENT DOCUMENTS

| | | |
|---|---|---|
| 1,799,463 A | 4/1931 | Hein |
| 1,850,273 A | 3/1932 | Thayer |
| 2,052,616 A | 12/1935 | Gardes |
| 2,578,394 A | 12/1951 | Stanley |
| 2,592,381 A | 4/1952 | Blackman |
| 2,602,447 A | 7/1952 | Paul |
| 2,607,342 A | 8/1952 | Abel |
| 3,176,595 A | 4/1965 | Schwartz |
| 3,354,882 A | 11/1967 | George |
| 3,450,134 A | 6/1969 | Willgerodt |
| 3,577,850 A | 5/1971 | Harris, Sr. |
| 3,892,512 A | 7/1975 | Diehl |
| 3,981,956 A | 9/1976 | Redmer et al. |
| 3,985,133 A | 10/1976 | Jenkins et al. |
| 4,044,757 A | 8/1977 | McWhorter et al. |
| 4,044,765 A * | 8/1977 | Kline ............... A61M 25/0662 |
| 4,074,715 A | 2/1978 | Geiger |
| 4,076,285 A | 2/1978 | Martinez |
| 4,089,335 A | 5/1978 | Harris |
| 4,184,836 A | 1/1980 | Rees |
| 4,201,209 A | 5/1980 | LeVeen et al. |
| 4,214,507 A | 7/1980 | Hock et al. |
| 4,381,275 A | 4/1983 | Sorensen |
| 4,385,025 A | 5/1983 | Salerno et al. |
| 4,389,271 A | 6/1983 | Shandy et al. |
| 4,397,706 A | 8/1983 | Allen et al. |
| 4,398,989 A | 8/1983 | Allen et al. |
| 4,431,031 A * | 2/1984 | Ettlinger ............... F16L 11/086 138/109 |
| 4,447,229 A | 5/1984 | Butterfield |
| 4,450,079 A | 5/1984 | Farr |
| 4,485,065 A | 11/1984 | Hatakeyama et al. |
| 4,512,486 A | 4/1985 | Kobayashi et al. |
| 4,543,093 A | 9/1985 | Christinger |
| 4,554,125 A | 11/1985 | Knapp |
| 4,585,435 A * | 4/1986 | Vaillancourt ....... A61M 5/1408 604/126 |
| 4,605,396 A | 8/1986 | Tseo et al. |
| 4,662,868 A | 5/1987 | Cambio, Jr. |
| 4,701,165 A | 10/1987 | DeHaitre |
| 4,803,031 A | 2/1989 | Ochs et al. |
| 4,850,980 A | 7/1989 | Lentz et al. |
| 4,957,682 A | 9/1990 | Kobayashi et al. |
| 4,986,820 A | 1/1991 | Fischer |
| 4,997,423 A | 3/1991 | Okuda et al. |
| 5,007,904 A | 4/1991 | Densmore et al. |
| 5,009,587 A | 4/1991 | Corvaglia et al. |
| 5,009,646 A | 4/1991 | Sudo et al. |
| 5,047,012 A | 9/1991 | Leuschner et al. |
| 5,279,606 A | 1/1994 | Haber et al. |
| 5,314,415 A | 5/1994 | Liebert et al. |
| 5,314,416 A | 5/1994 | Lewis et al. |
| 5,460,625 A * | 10/1995 | Johnson ............... A61M 39/08 604/403 |
| 5,484,566 A | 1/1996 | Gabbard |
| 5,507,766 A * | 4/1996 | Kugo ............... A61M 25/0053 |
| 5,529,738 A | 6/1996 | Mercereau |
| 5,651,998 A | 7/1997 | Bertschi et al. |
| 5,902,276 A | 5/1999 | Namey, Jr. |
| 5,993,422 A | 11/1999 | Schafer |
| 6,004,300 A | 12/1999 | Butcher et al. |
| 6,090,081 A | 7/2000 | Sudo et al. |
| 6,165,402 A | 12/2000 | Gabbard et al. |
| 6,208,885 B1 | 3/2001 | Young et al. |
| 6,312,423 B1 | 11/2001 | Ota et al. |
| 6,322,739 B1 | 11/2001 | Andersson et al. |
| 6,342,120 B1 | 1/2002 | Basta |
| 6,494,866 B1 | 12/2002 | Robinson |
| 6,562,009 B1 | 5/2003 | Schottli |
| 6,607,685 B2 | 8/2003 | Naritomi et al. |
| 6,817,990 B2 | 11/2004 | Yap et al. |
| 6,902,210 B1 | 6/2005 | Rowley |
| 7,041,081 B2 | 5/2006 | Minezaki et al. |
| 7,111,848 B2 | 9/2006 | Tachikawa et al. |
| 7,166,089 B2 | 1/2007 | Huang |
| 7,195,609 B2 | 3/2007 | Huegli |
| 7,229,276 B2 | 6/2007 | Chiba |
| 7,374,802 B2 | 5/2008 | Zihlmann |
| 7,618,276 B2 | 11/2009 | Paglia et al. |
| 8,066,688 B2 | 11/2011 | Zinger et al. |
| 8,277,714 B1 | 10/2012 | Blue et al. |
| 2003/0030186 A1 | 2/2003 | Riiska et al. |
| 2003/0039717 A1 | 2/2003 | Hwang et al. |
| 2003/0153876 A1 | 8/2003 | Kirchhofer et al. |
| 2004/0099994 A1 | 5/2004 | Brinkhues |
| 2004/0100093 A1 | 5/2004 | Leigh-Monstevens |
| 2004/0161489 A1 | 8/2004 | Hwang et al. |
| 2004/0210187 A1 | 10/2004 | Zawacki |
| 2005/0115624 A1* | 6/2005 | Walak ............... 138/139 |
| 2005/0182371 A1 | 8/2005 | Wagner et al. |
| 2005/0234522 A1 | 10/2005 | Ley et al. |
| 2006/0069356 A1 | 3/2006 | Witowski |
| 2006/0079856 A1 | 4/2006 | Smith et al. |
| 2006/0170134 A1 | 8/2006 | Rowley et al. |
| 2006/0204074 A1 | 9/2006 | Moriya et al. |
| 2007/0060896 A1 | 3/2007 | Miller et al. |
| 2007/0073223 A1 | 3/2007 | Huang |
| 2007/0215268 A1 | 9/2007 | Pingleton et al. |
| 2007/0219507 A1 | 9/2007 | Dai et al. |
| 2007/0246573 A1 | 10/2007 | Jaunay |
| 2008/0065023 A1 | 3/2008 | Kennard |
| 2008/0284167 A1 | 11/2008 | Lim et al. |
| 2008/0302437 A1 | 12/2008 | Lovett et al. |
| 2009/0126820 A1 | 5/2009 | Thomas et al. |
| 2010/0022966 A1 | 1/2010 | Kennard |
| 2010/0063481 A1 | 3/2010 | Hoffman et al. |
| 2010/0076406 A1 | 3/2010 | Raulerson |
| 2010/0130922 A1 | 5/2010 | Borlaug et al. |
| 2010/0145313 A1* | 6/2010 | Packard ............. A61M 25/0012 604/535 |
| 2010/0176584 A1* | 7/2010 | Ito ............... A61M 39/10 |
| 2011/0127186 A1 | 6/2011 | Enns et al. |
| 2011/0306826 A1 | 12/2011 | Franklin et al. |
| 2012/0022403 A1 | 1/2012 | Noble et al. |
| 2012/0024411 A1 | 2/2012 | Hahn et al. |
| 2012/0041425 A1 | 2/2012 | Tsunematsu |
| 2012/0216903 A1* | 8/2012 | Osborne ............. 138/137 |

FOREIGN PATENT DOCUMENTS

| | | |
|---|---|---|
| EP | 2158935 B1 | 7/2014 |
| EP | 2422837 B1 | 12/2014 |
| JP | S52-020687 | 2/1977 |
| JP | 2007503262 A | 2/2007 |
| JP | 200873530 | 4/2008 |
| JP | 2008073530 A | 4/2008 |
| JP | 2010511482 A | 4/2010 |

(56) References Cited

FOREIGN PATENT DOCUMENTS

| JP | 2013530014 A | 7/2013 |
|----|--------------|--------|
| WO | 9010816 A1 | 9/1990 |
| WO | 2005021069 A1 | 3/2005 |
| WO | 2008070220 A1 | 6/2008 |
| WO | 2010122988 A1 | 10/2010 |
| WO | 2012005908 A2 | 1/2012 |

OTHER PUBLICATIONS

"Jun. 20, 2016_Extended_ESR_EP138442900_Jun. 16, 2016".

* cited by examiner

OVERMOLDED MEDICAL CONNECTOR TUBING AND METHOD

BACKGROUND OF THE INVENTION

Field of the Invention

The present invention is related to the medical field and, in particular, medical tubing used in the medical field to conduct fluids to and from a patient and/or between medical equipment which may comprise one or more end connectors for making fluid connections to conduct fluids to and from patients and medical equipment.

Description of Related Art

Numerous examples of medical tubing and connectors therefor may be found in the medical field. For example, U.S. Patent Application Publication No. 2012/0024411 to Hahn et al. is generally directed to tubing for use in connecting components of liquid chromatography and other analytical systems and discloses tubing that is comprised of three distinct portions, including an outer layer, an inner layer, and a passageway defined by the inner layer. The tubing includes a retention feature, such as a barb, machined onto the end of the outer layer. The inner layer protrudes from the barb, and the barb and the protruding portion of the inner layer are overmolded together with a tip.

U.S. Patent Application No. 2011/0306826 to Franklin et al. discloses an implantable device for use in a medical system to protect tubing from puncture. In one embodiment, a shielding device is provided that is overmolded onto a tube or is overmolded to a housing connected to the tube end as well as the tube.

U.S. Patent Application No. 2011/0127186 to Enns et al. discloses packaging tubes for elongate medical devices, such as catheters and guide wires, in which a series of plastic clips are overmolded onto a tube. Each of the clips surrounds adjacent sections of the tube such that each clip forms a closed loop, surrounding the outer surface of the tube at each section where the clip is located.

U.S. Patent Application Publication No. 2010/0130922 to Borlaug et al. discloses a medical fluid injection device comprising fluid connectors that are made of an overmolded, thermoplastic elastomer.

U.S. Patent Application Publication No. 2010/0063481 to Hoffman et al. discloses flow path assemblies for use in a fluid path for delivery of medical fluids. This publication discloses tubing connected to a syringe outlet at one end and has a compressible sealing element connected to the opposing end. The sealing element may be formed of an elastomeric material, and is generally cylindrical in shape and dimensioned to be concentric with the tubing. The elastomeric sealing element may be overmolded onto the tubing to eliminate the need for an adhesive.

U.S. Patent Application Publication No. 2010/0022966 to Kennard discloses a fluid delivery device that includes tubing with an overmolded region, and a barbed connector end may be secured to the overmold region by way of a compression fit thereto.

U.S. Patent Application Publication No. 2008/0284167 to Lim et al. discloses fittings for connecting tubing. In one embodiment, the fitting is formed by injection molding, and then material is overmolded or co-molded over the fitting to form an extension portion, and a tube end is then inserted into the fitting to conduct fluid through the fitting.

U.S. Patent Application Publication No. 2007/0215268 to Pingleton discloses a method of applying a braid to a tube, and fusing of the braid to the tube to prevent kinking thereof, etc. The braid may be insert-molded or over-molded to the tube.

U.S. Patent Application Publication No. 2006/0170134 to Rowley et al. discloses a method of injection over-molding a connector with a tubing segment.

SUMMARY OF THE INVENTION

One embodiment described herein is directed to a high pressure medical connector tubing assembly comprising a tube element comprising opposed tube ends and a passageway therethrough, an end element overmolded to at least one of the opposed tube ends, the end element comprising an annular end portion having a preselected length, and a connector element comprising a connector hub defining a receiving cavity, the tube end with the overmolded end element fixedly secured in the receiving cavity. The preselected length of the annular end portion may be used to pre-control the axial location of stress concentration in the connector hub.

The tube end with the overmolded end element may be fixedly secured in the receiving cavity by solvent bonding. The end element may be formed with at least one external indicator to visibly identify depth of insertion of the tube end with the overmolded end element in the receiving cavity. The tube element may comprise braided tubing formed of an inner braid encapsulated by a flexible polymer layer. The connector element may comprise a connector port defining a fluid passageway. The annular end portion may define a tapered entranceway tapering from the fluid passageway to the passageway in the tube element. The entranceway may taper inwardly at an angle of, for example, between 0° and 80°. An end element is overmolded to each of the tube ends of the tube element. The connector element may comprise a pair of connector elements, and the tube ends each having an overmolded end element fixedly secured, respectively, in the receiving cavities of the connector elements. The tube element may comprise braided tubing formed of an inner braid encapsulated by a flexible polymer layer.

Another embodiment is directed to a method of forming a high pressure medical connector tubing assembly, comprising providing a tube element comprising opposed tube ends and a passageway therethrough, overmolding an end element onto at least one of the opposed tube ends, the end element comprising an annular end portion having a preselected length, providing a connector element comprising a connector hub defining a receiving cavity, and securing the tube end with the overmolded end element in the receiving cavity. The preselected length of the annular end portion may be used to pre-control the axial location of stress concentration in the connector hub.

Securing the tube end with the overmolded end element in the receiving cavity may comprise solvent bonding. The end element may be formed with at least one external indicator to visibly identify depth of insertion of the tube end with the overmolded end element in the receiving cavity. The tube element may comprise braided tubing formed of an inner braid encapsulated by a flexible polymer layer. The connector element may comprise a connector port defining a fluid passageway. The annular end portion may define a tapered entranceway tapering from the fluid passageway to the passageway in the tube element. The entranceway may taper inwardly at an angle of, for example, between 0° and 80°. An end element may be overmolded to each of the tube ends of the tube element. The tube ends may each have an overmolded end element and are fixedly secured, respectively, in the receiving cavities of the connector elements. The tube element may comprise braided tubing formed of an inner braid encapsulated by a flexible polymer layer.

Further details and advantages of the present invention will be understood from the following detailed description read in conjunction with the accompanying drawings.

DESCRIPTION OF THE PREFERRED EMBODIMENTS

For purposes of the description hereinafter, spatial orientation terms, as used, shall relate to the referenced embodiment as it is oriented in the accompanying drawing figures or otherwise described in the following detailed description. However, it is to be understood that the embodiments described hereinafter may assume many alternative variations and configurations. It is also to be understood that the specific components, devices, features, and operational sequences illustrated in the accompanying drawing figures and described herein are simply exemplary and should not be considered as limiting.

Figure 1A:
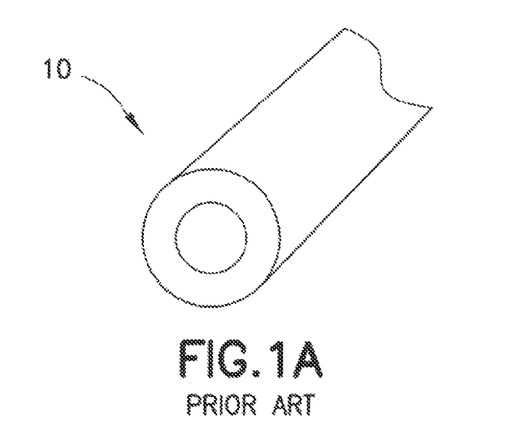
FIGS. 1A-1C are perspective end views of known medical tubing used in the medical field.
Figure 1B:
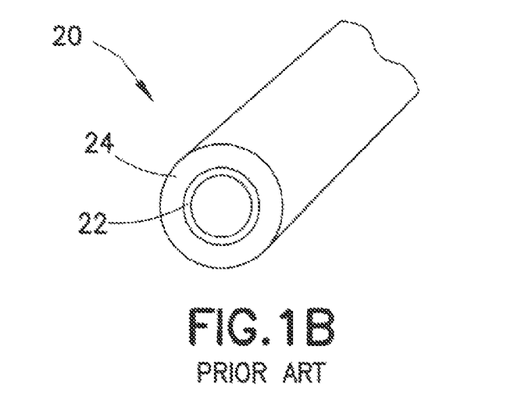
Figure 1C:
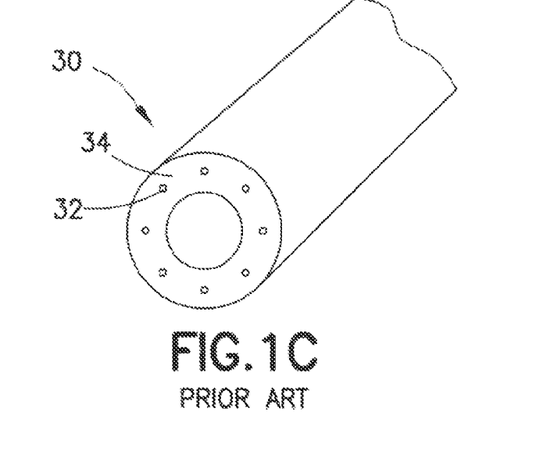

Referring to FIGS. 1A-1C, in the medical field, there are several available options for high pressure tubing with connector ends. In FIG. 1A, medical tubing 10 is shown in the form of high pressure PVC tubing. In this known configuration, production costs are considered to be low once dedicated, but expensive, production injection molding tooling is in place. The medical tubing 10 relies on a single wall plastic polymer that incorporates a plasticizer to make the tube non-rigid. Such plasticizers are under scrutiny in the medical field for biocompatibility and possible migration into the fluid path. Additionally, operating pressures are usually limited to 1000 psi due to the lower tensile strength of the PVC versus engineering grade plastics. In typical applications, luer hubs may be solvent-bonded to the ends of the medical tubing 10. Solvent bonding is known to cause luer stress crazing and cracking issues, wherein fine cracks appear in the surface of the luer hubs when the luer hubs are solvent-bonded to the ends of the medical tubing 10. This induced cracking is due to high stresses developed with high durometer rigid tubing when end connectors are applied to the ends of the medical tubing 10 which require interference fits and solvent-bonding. These interference fits and accompanying solvent bonding attack can lead to air ingress and or pressure failures. Ultraviolet (UV) adhesive bonding is not a reliable alternative to solvent bonding because the plasticizer attacks the UV adhesive and can de-laminate the bonded joint after sterilization. Luer connector fittings may be insert-molded onto the ends of the medical tubing 10, but production costs increase and connector geometry is limited to simple in-line fluid paths.

In FIG. 1B, medical tubing 20 in the form of coextruded high pressure connector tubing is shown. The medical tubing 20 has a high strength inner wall 22 formed of a suitable polymer which is coaxially surrounded by a flexible outer wall 24 formed of another polymer so that the medical tubing can achieve a 1200 psi rating, but retains a certain degree of flexibility. In this embodiment, luer hubs may be solvent-bonded to the ends of the medical tubing 20, but direct solvent bonding to the medical tubing 20 also causes luer hub stress crazing and cracking issues in a similar manner to the foregoing medical tubing 10. This induced cracking is due to high stresses developed with medium aggregate durometer tubing when end connectors are applied to the ends of the medical tubing 20 which require interference fits and solvent-bonding. These interference fits and accompanying solvent bonding attack can lead to air ingress and or pressure failures. Again, Ultraviolet (UV) adhesive bonding is not a reliable alternative to solvent bonding because the UV adhesive requires a clearance between the medical tubing 20 and luer hub for optimum strength and shelf life is limited due to adhesive bond breakdown over time. Luer connector fittings may be insert-molded onto the ends of the medical tubing 20 but, again, production costs increase and connector geometry is limited to simple in-line fluid paths.

In FIG. 1C, medical tubing 30 in the form of braided high pressure connector tubing is shown. The medical tubing 30 has a high strength inner braid 32 formed of a suitable polymer that is encapsulated by a flexible polymer layer 34 to achieve a 1200 psi pressure rating with a high grade flexibility. The inner braid 32 keeps the medical tubing 30 from swelling and rupturing, but can inhibit visual fluid path clarity, often used to ensure air bubble visualization after air-purging operations. Additionally, when the braided medical tubing 30 is cut, it is desirable to isolate the cut ends from high pressures to keep the fluid pressure from wicking into the braid which can cause a pressure failure of the medical tubing 30. As in the previously discussed embodiments, direct solvent bonding can cause luer hub stress crazing and cracking issues. This induced cracking is due to high stresses developed when end connectors are applied to the ends of medical tubing 30 and which require interference fits and solvent-bonding. Stress is high due to the level of interference needed to squeeze the braided medical tubing 30 into a luer hub and needed to keep pressurized liquid from wicking into the braid ends which can cause a pressure failure of the medical tubing 30. Again, Ultraviolet (UV) adhesive bonding is not a reliable alternative to solvent bonding because the UV adhesive requires a clearance between the medical tubing 30 and luer hub for optimum strength, and shelf life is limited due to adhesive bond breakdown over time. Luer connector fittings may be insert-molded onto the ends of the medical tubing 30 but, again, production costs increase and connector geometry is limited to simple in-line fluid paths.

Figures 2, 3:
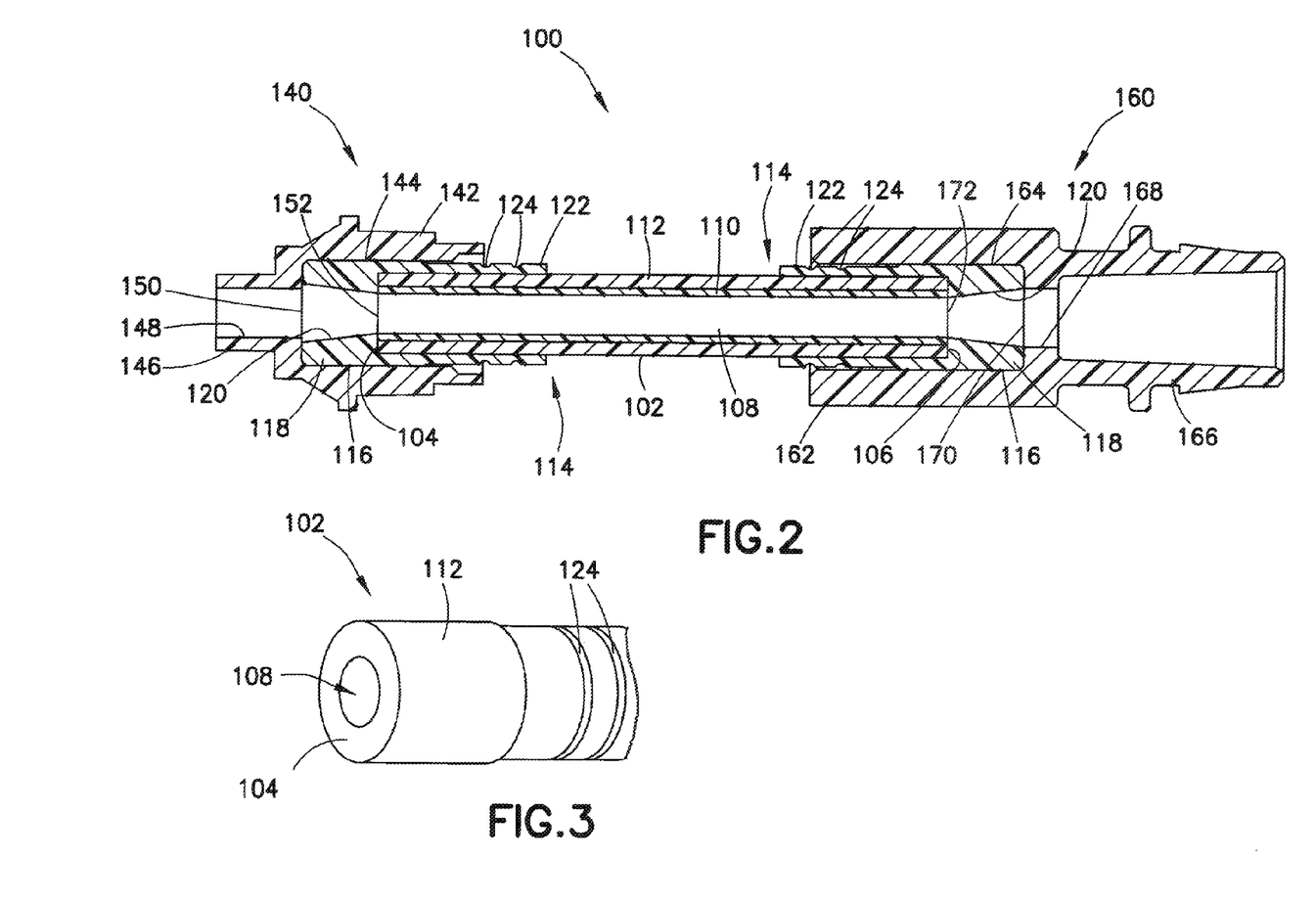
FIG. 2 is a cross-sectional view of an overmolded medical connector tubing assembly according to one embodiment.
FIG. 3 is an isometric view of an end portion of a tube element used in the medical connector tubing assembly shown in FIG. 2.

Referring to FIGS. 2-3, a high pressure medical connector tubing assembly 100 according to one embodiment (hereinafter "connector tubing 100") is shown. The connector tubing 100 generally comprises a tube element 102 which may be a coextruded or braided tube element according to known tubing elements found in the medical field. The tube element 102 comprises opposed tube ends 104, 106 and a defined central passageway 108 for conducting fluid therethrough. The tube element 102 comprises braided tubing in the depicted embodiment. The tube element 102 comprises a high strength inner braid 110 formed of a suitable polymer that is encapsulated by a flexible polymer layer 112 to achieve a 1200 psi pressure rating with a high grade flexibility.

With the tube element 102 present, end pieces or elements 114 may be applied to the opposing tube ends 104, 106 of the tube element 102 to form a composite structure. The end elements 114 each comprise annular or tubular bodies 116 having annular or tube-shaped end portions 118 and are overmolded, respectively, to the opposing tube ends 104, 106 of the tube element 102. The tubular bodies 116 of the end elements 114 may be made of soft plastic material, such as polyurethane or any flexible thermoplastic material that is compatible with the underlying tube element 102, to facilitate overmolding to the tube ends 104, 106 of the tube element 102. Each of the tubular bodies 116 may be molded such that the end portions 118 define tapered entranceways 120 formed with a predetermined transition or taper angle, such as between 0° and 80° as examples. An exterior surface 122 of the tubular body 116 of each of the end elements 114 may be formed with one or more external indicators 124, such as an annular grooves and the like, to indicate desired or indicated insertion points or distances for the composite tube ends 104, 106 having overmolded end elements 114 into mating or receiving connector elements 140, 160, as described herein. The overmolded end elements 114 are advantageous in one respect in that, when applied, the end elements 114 seal the cut tube ends 104, 106 of the tube element 102. When the braided medical tubing comprising the tube element 120 is cut, it is desirable to isolate the cut ends from high pressures to keep the fluid pressure from wicking into the braid which can cause a pressure failure of the tube element 120. The overmolded end elements 114 are advantageous in that, when applied, the end elements 114 seal the cut tube ends 104, 106 of the braided tube element 102.

As indicated, connector elements 140, 160 are applied, respectively, to the opposed composite tube ends 104, 106 of the tube element 102 having the overmolded end elements 114. The connector elements 140, 160 may be conventional injection molded luer connectors that are well-known in the medical field and the following discussion of specific features of the connector elements 140, 160 is intended to be as non-limiting as to possible luer connector elements or end configurations that may be used with the tube element 102. Moreover, any specific discussion hereinafter directed to one of the connector elements 140, 160 is equally applicable to the opposed connector element 140, 160 and the concepts described herein may further be applicable to any suitable known luer connector elements known in the medical field. The specific configurations of the connector elements 140, 160 shown in FIGS. 2 and 3-8 are intended only to be exemplary.

The connector element 140 comprises a connector hub 142 defining a receiving recess or cavity 144 to receive the composite tube end 104 with overmolded end element 114. The connector hub 142 may comprise a connector port or portion 146 adapted for connection to an upstream or downstream fluid conducting element (not shown). As shown in FIG. 2, the tapered entranceway 120 defined by the end portion 118 of the overmolded end element 114 is formed at a transition or taper angle of any suitable angle, such as between and 0° and 80° as examples, to permit smooth fluid transition between a fluid passageway 148 in the connector port 146 and the tapered entranceway 120 and between the tapered entranceway 120 and the central passageway 108 in the tube element 102. The tapered entranceway 120 desirably maintains laminar flow conditions at a first transition point or seam 150 between the fluid passageway 148 and the end portion 118 of the overmolded end element 114 defining the tapered entranceway 120, as well as at a second transition point or seam 152 between the end portion 118 of the overmolded end element 114 defining tapered entranceway 120 and the central passageway 108 in the tube element 102. The tapered entranceway 120 generally provides a smooth transition between the between the fluid passageway 148 in the connector port 146 to the central passageway 108 in the tube element 102 and helps minimize possible air traps or stagnation points by providing a smooth transition for fluid at the first transition point or seam 150 between the fluid passageway 148 and the tapered entranceway 120 defined by end portion 118 of the overmolded end element 114, as well as at the second transition point or seam 152 between the tapered entranceway 120 defined by end portion 118 and the central passageway 108 in the tube element 102. The composite tube end 104 of the tube element 102 having the overmolded end element 114 may be secured in the receiving recess or cavity 144 by solvent bonding and like joining methods, such as laser welding. The external indicators 124 on the tubular body 116 of the end element 114 disposed on the tube end 104 of the tube element 102 provide a visible indication of insertion to a desired insertion depth of the composite tube end 104 and overmolded end element 114 into the receiving cavity 144 of the connector element 140 and, further, visibly validate a solvent-bonded, interference fit between the end element 114 and the connector element 140 as well as helping to prevent under-insertion of the composite tube end 104 and overmolded end element 114 into the receiving cavity 144. An interference-fit, solvent-bond connection is desirably present between the composite tube end 104 and overmolded end element 114 and the receiving cavity 144 of the connector element 140.

The connector element 160 comprises a connector hub 162 defining a receiving recess or cavity 164 to receive the opposing composite tube end 106 with overmolded end element 114. The connector hub 162 may comprise a connector port or portion 166 adapted for connection to an upstream or downstream fluid conducting element (not shown). As shown in FIG. 2, the tapered entranceway 120 defined by the end portion 118 of the overmolded end element 114 is formed at a transition or taper angle of any suitable angle, 0° and 80° as examples, to permit smooth fluid transition between a fluid passageway 168 in the connector port 166 and the tapered entranceway 120 and between the tapered entranceway 120 and the central passageway 108 in the tube element 102. The tapered entranceway 120 desirably maintains laminar flow conditions at a first transition point or seam 170 between the fluid passageway 168 and the end portion 118 of the overmolded end element 114 defining the tapered entranceway 120, as well as at a second transition point or seam 172 between the end portion 118 of the overmolded end element 114 defining tapered entranceway 120 and the central passageway 108 in the tube element 102. The tapered entranceway 120 generally provides a smooth transition between the between the fluid passageway 168 in the connector port 166 to the central passageway 108 in the tube element 102 and helps minimize possible air traps or stagnation points by providing a smooth transition for fluid at the first transition point or seam 170 between the fluid passageway 148 and the tapered entranceway 120 defined by end portion 118 of the overmolded end element 114, as well as at the second transition point or seam 172 between the tapered entranceway 120 defined by end portion 118 and the central passageway 108 in the tube element 102. The composite tube end 106 of the tube element 102 having the overmolded end element 114 may be secured in the receiving recess or cavity 164 by solvent bonding and like joining methods, such as laser welding. The external indicators 124 on the tubular body 116 of the end element 114 disposed on the tube end 106 of the tube element 102 provide a visible indication of insertion to a desired insertion depth of the composite tube end 106 and overmolded end element 114 into the receiving cavity 164 of the connector element 160 and, further, visibly validate a solvent-bonded, interference fit between the end element 114 and the connector element 160 as well as helping to prevent under-insertion of the composite tube end 106 and overmolded end element 114 into the receiving cavity 164. An interference-fit, solvent-bond connection is desirably present between the composite tube end 104 and overmolded end element 114 and the receiving cavity 164 of the connector element 160.

Figure 4:
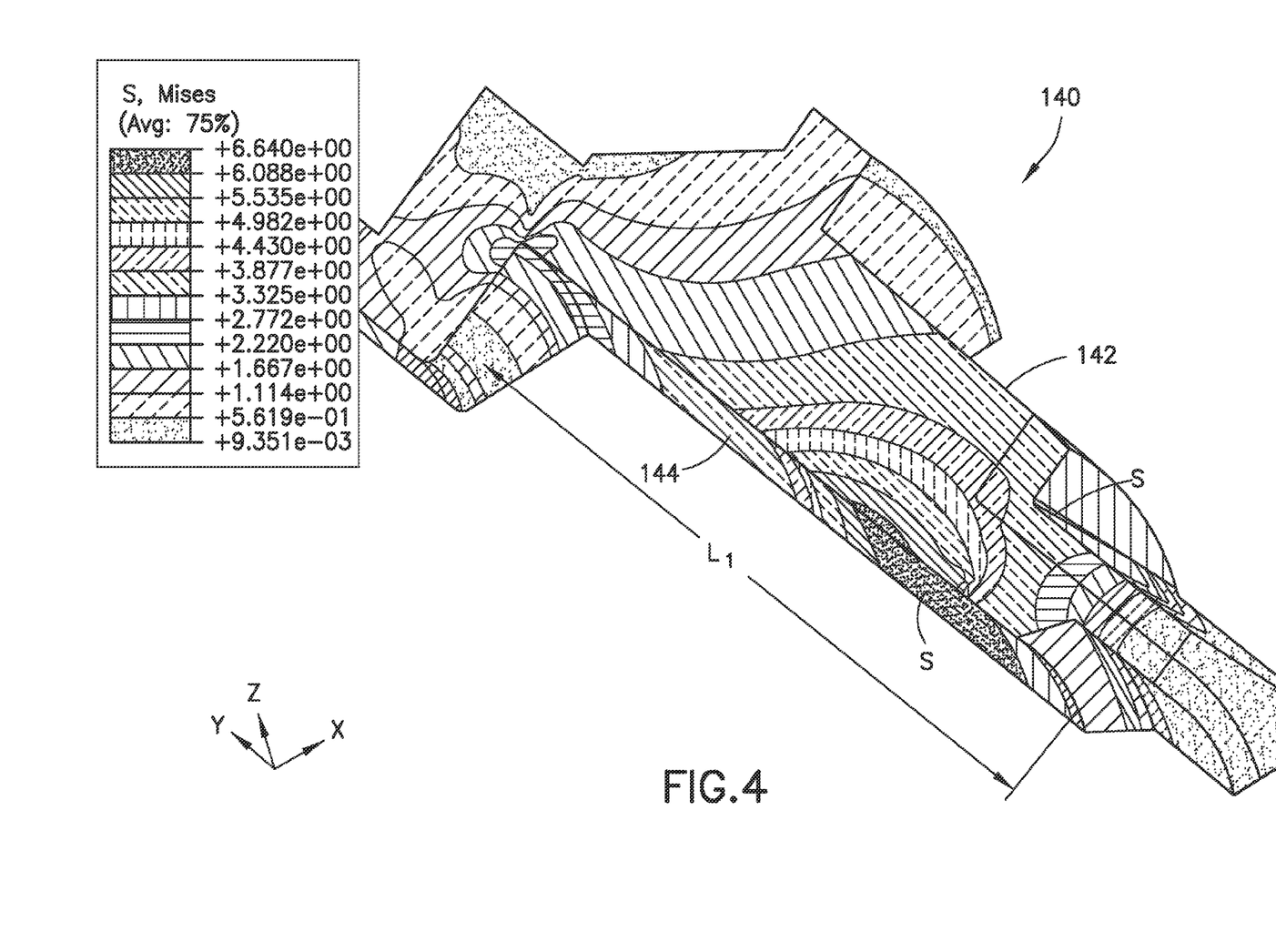
FIG. 4 is a Finite Element Analysis (FEA) plot of an exemplary connector element of the medical connector tubing assembly shown in FIG. 2 once assembled with an overmolded tube element.

Referring further to FIG. 4, a finite element analysis (FEA) plot is shown of the connector element 140 having the tube end 104 and overmolded end element 114 assembled in the receiving cavity 144 of the connector element 140 and secured therein by an interference-fit, solvent bond connection In FIG. 4, the FEA plot of the connector hub 142 of the connector element 140 shows a location of stress concentration S in the connector hub 142 once the composite tube end 104 and overmolded end element 114 is seated and secured into the receiving cavity 144 of the connector element 140. The position or location of stress concentration S may be altered in an axial direction along the connector hub 142, according to this disclosure, to be positioned or located at preselected axial locations along an axial length $L_1$ in the receiving cavity 144 of the connector hub 142. This axial position may be preselected or "pre-controlled" to locate the area of stress concentration S substantially at any desired position along the axial length $L_1$, and typically at locations away from stress risers, such as hard interfaces, corners, edges, sharp or prominent surface features, or material thin areas. In this manner, stress concentration S in the connector hub 142 may be set at preselected or "pre-controlled" axial locations and, thus, the stress concentrations in the connector element 140 may be "pre-controlled" in advance. Such stress concentrations S can induce crazing and cracking in the connector hub 142 when the tube end 104 and overmolded end element 114 are assembled in the receiving cavity 144 and the tube element 102 is repeatedly pressurized. This disclosure provides a method and physical arrangement by which the location of stress concentration S may be preselected or "pre-controlled" so as to be located at a preselected axial location along the connector hub 142 so as to avoid stress riser at hard interfaces, corners, edges, sharp or prominent surface features, or material thin areas, and be located at axial locations along the connector hub 142 having more "planar" surface features and generally free of the foregoing stress-inducing features.

Figure 5:
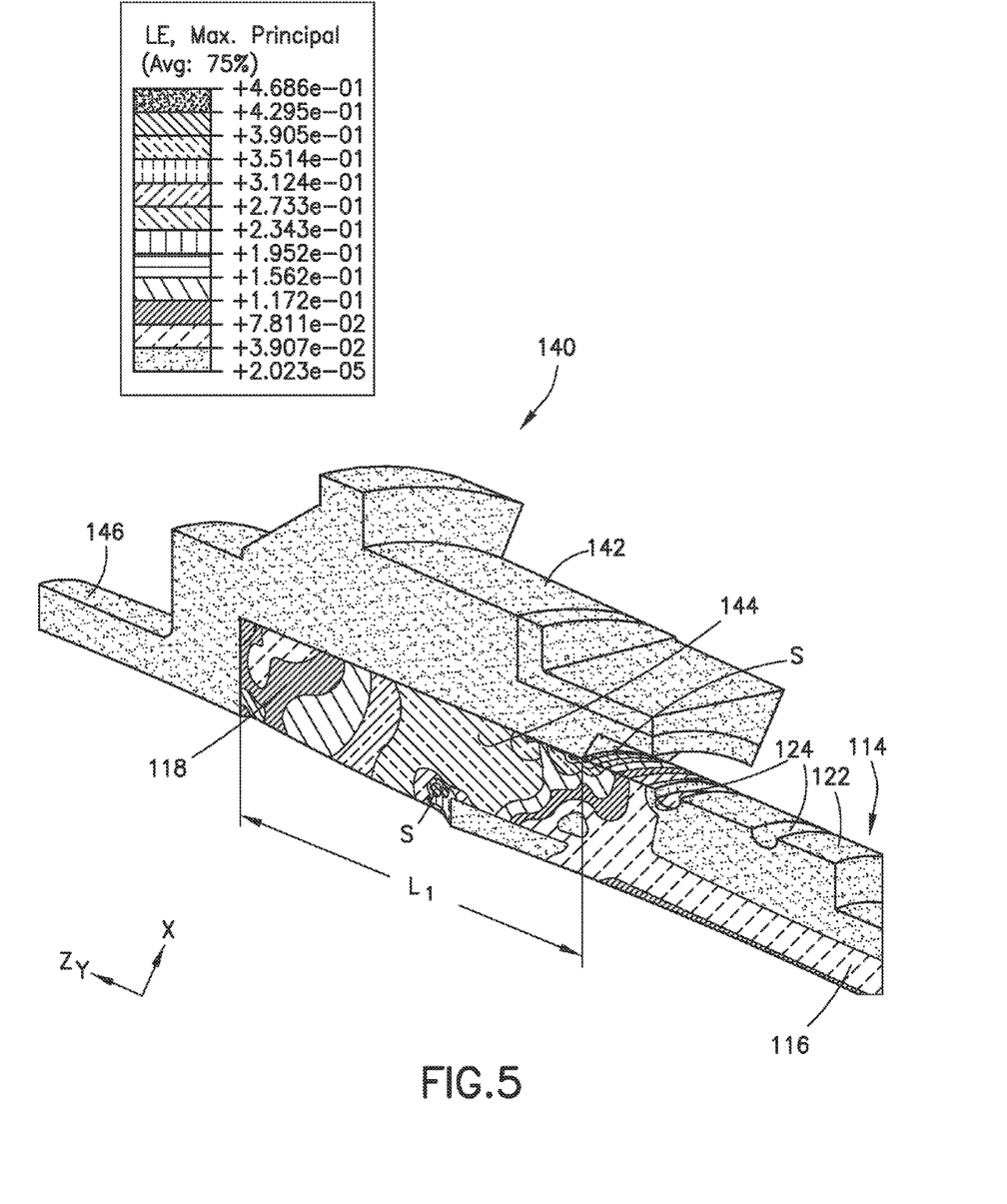
FIG. 5 is a Finite Element Analysis (FEA) plot of the assembled connector element and tube element when under fluid pressure.

In FIG. 5, an FEA plot of the overmolded end element 114 is provided showing the overmolded end element 114 seated and secured in the receiving cavity 144 of the connector element 140. FIG. 5 shows the stress concentration S in the end element 114 when the internal tube element 102 is under pressure at approximately 1200 psi. The stress concentration S in the end element 114 is most prominent or at a maximum generally at the location where the tube end 104 seats of fits within the end element 114. In FIG. 5, when the tube element 102 is under pressure, the pressure stretches the tube element 102 and overmolded end element 114 on the tube end 104 within the connector hub 142 of the connector element 140. The tube end 104, while under pressure, should stay within the body of the connector hub 142 (e.g., within the receiving cavity 144) to prevent rupture, and this positioning is accomplished by preselecting or "pre-controlling" the axial positioning of the tube end 104 within the overmolded end element 114 and by preselecting the hardness of the material forming the overmolded end element 114.

As will be generally understood from an inspection of FIGS. 4-5 viewed together, the stress concentration S in the overmolded end element 114 is approximately radially coextensive with the stress concentration S in the connector hub 142 of the connector element 140 when assembled in the receiving cavity 144 and under pressure. Thus, preselecting or "pre-controlling" the location of stress concentration S in the overmolded end element 114 likewise preselects or "pre-controls" the location of stress concentration S in the connector hub 142 and this location is generally dependent upon the axial positioning of the tube end 104 within the overmolded end element 114. As noted previously, it desirable to preselect or "pre-control" the location of stress concentration S in the connector hub 142 so that this preselected or "pre-controlled" location avoids stress risers at hard interfaces, corners, edges, sharp or prominent surface features, or material thin areas and, alternatively, is located at axial locations along the connector hub 142 having "planar" surface features and generally free of the foregoing stress-inducing features.

Figure 6:
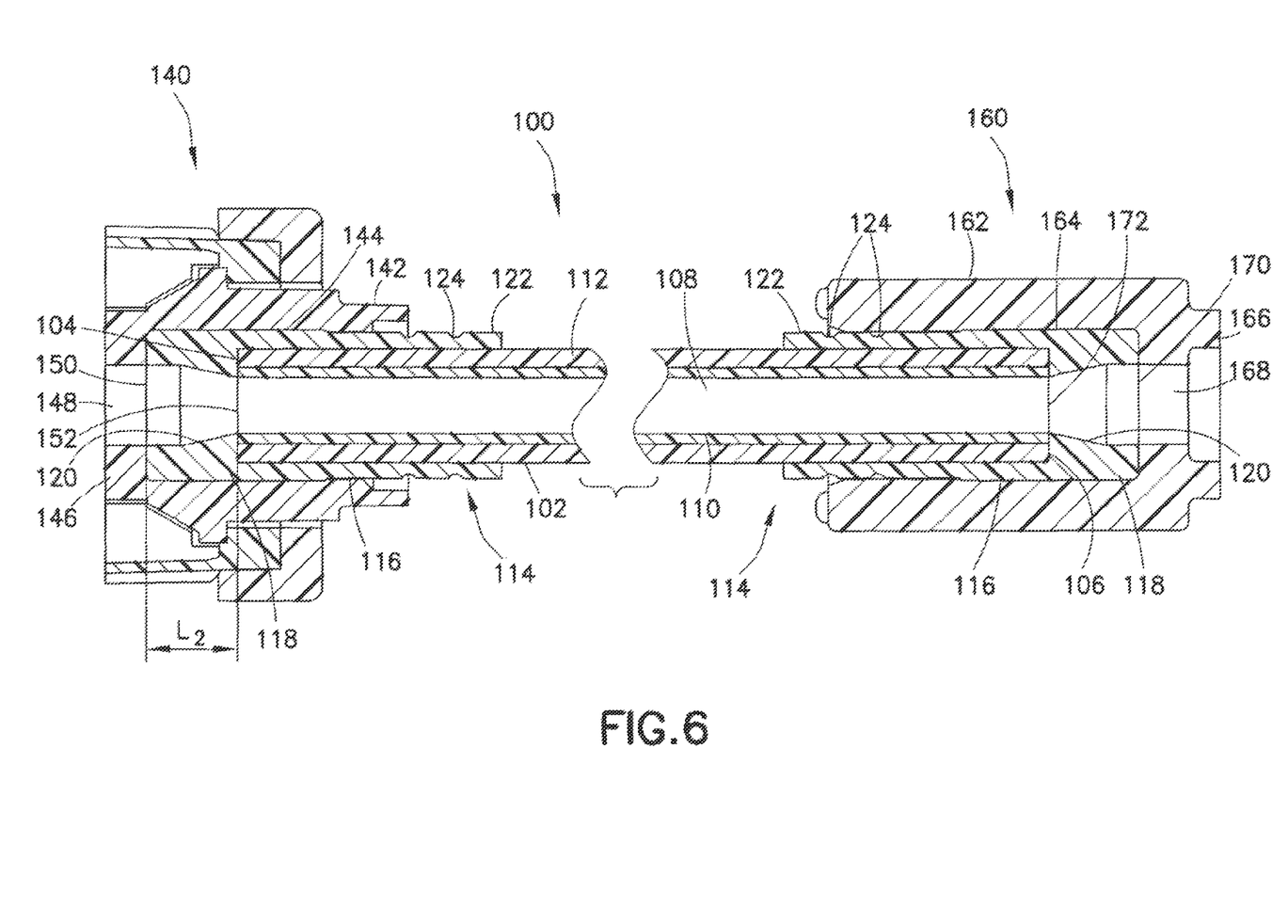
FIG. 6 is a cross-sectional view of the medical connector tubing assembly of FIG. 2 according to a first exemplary modification of the assembled connector element and tube element.
Figure 7:
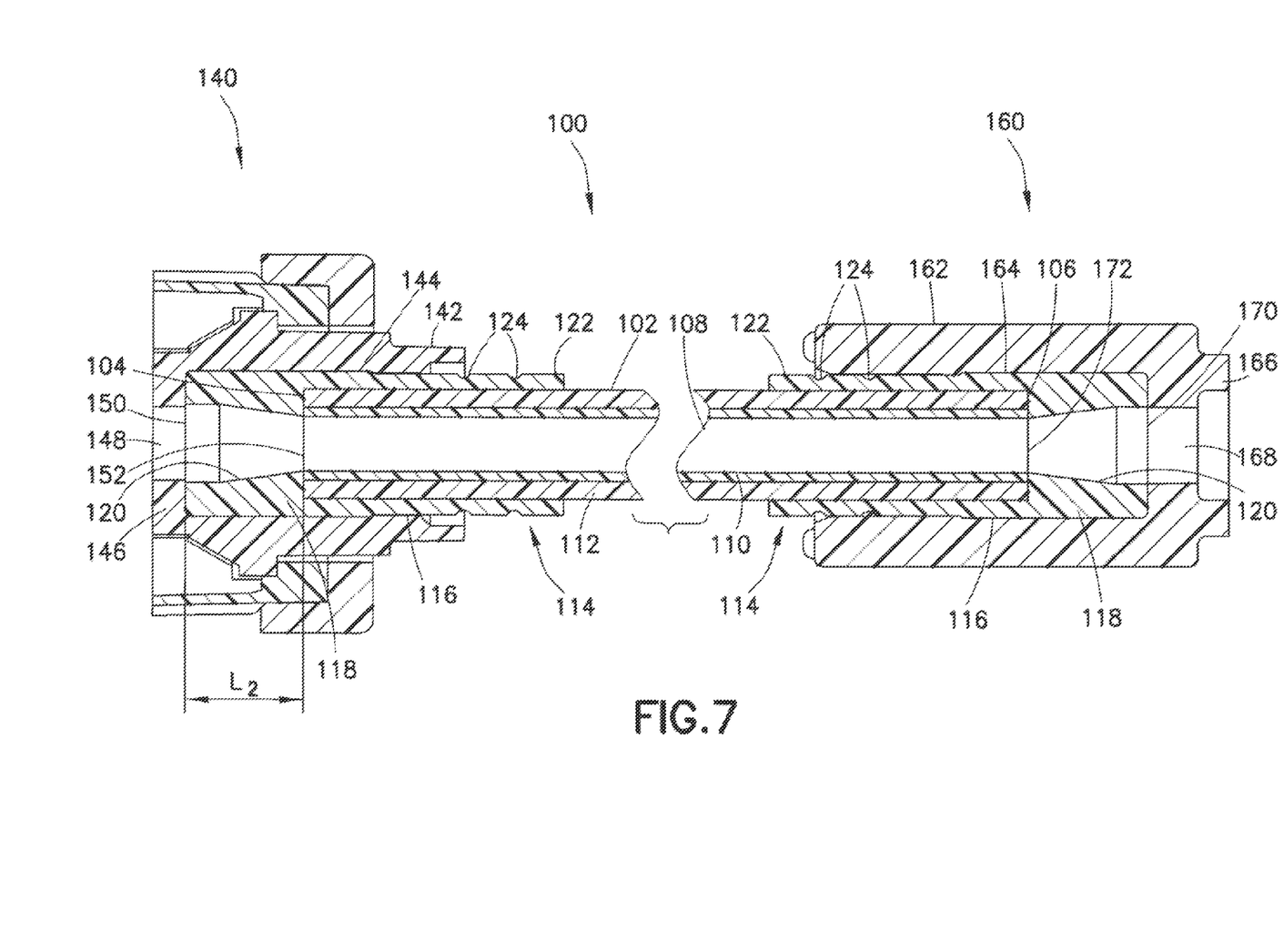
FIG. 7 is a cross-sectional view of the medical connector tubing assembly of FIG. 2 according to a second exemplary modification of the assembled connector element and tube element.
Figure 8:
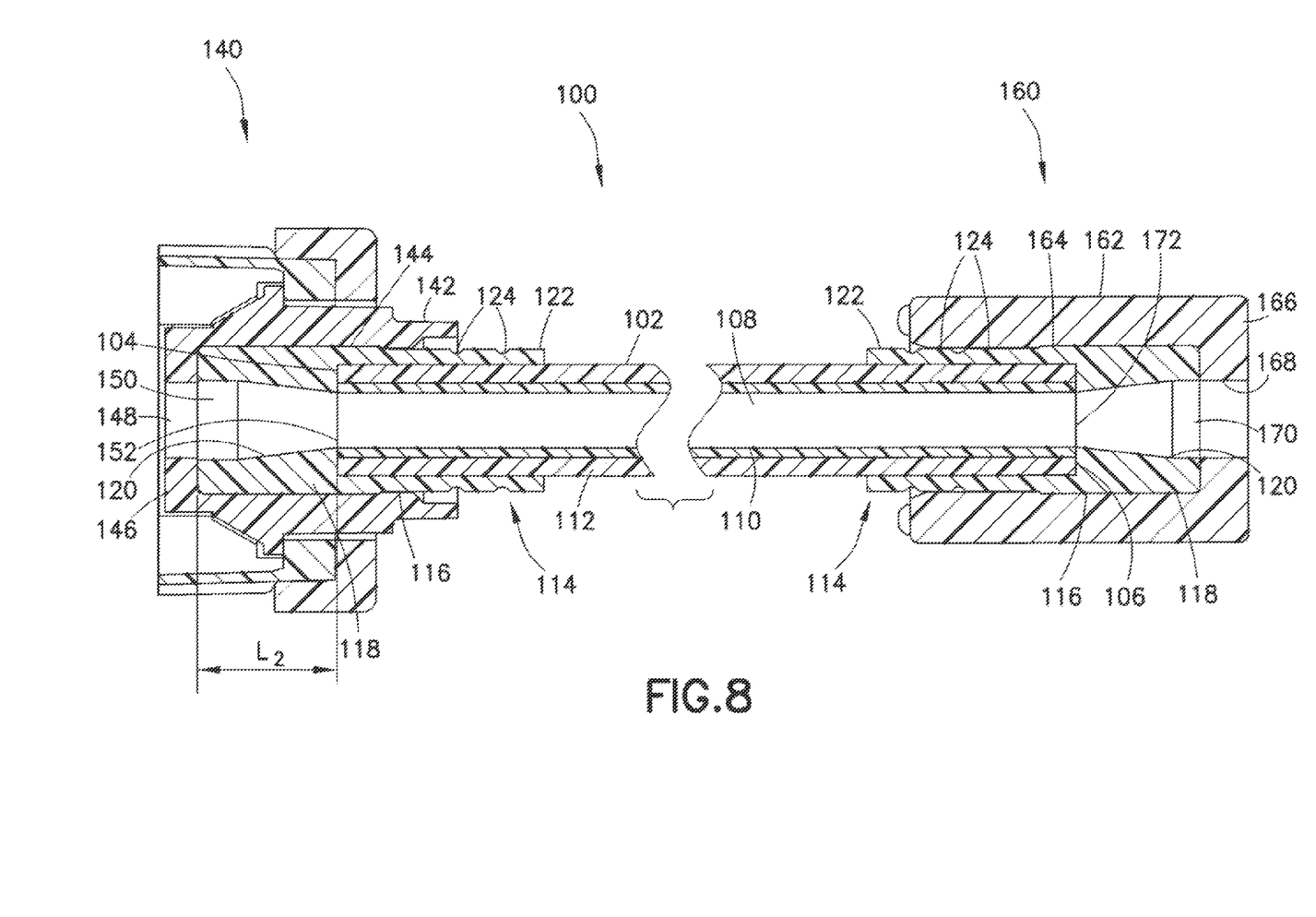
FIG. 8 is a cross-sectional view of the medical connector tubing assembly of FIG. 2 according to a second exemplary modification of the assembled connector element and tube element.

FIGS. 6-8 illustrate three (3) exemplary embodiments of the connector tubing 100 in which the tube end 104 is located at different axial positions within the overmolded end element 114, thereby changing the axial location of the stress concentration S in the overmolded end element 114 and, hence, the connector hub 142 located radially outward from the overmolded end element 114. As will be understood from viewing FIGS. 6-8 in sequence, the axial position of the tube end 104 within the overmolded end element 114 is changed by shortening or lengthening the axial length $L_2$ of the end portion 118 of the tubular body 116 of the end element 114. From FIGS. 6-8, it will be understood that the connector elements 140, 160 may have different configurations and the versions of the connector elements 140, 160 in FIGS. 2 and 6-8 are intended to be exemplary only. FIG. 6 shows the end portion 118 with the shortest axial length $L_2$ so that the axial position of the tube end 104 within the end element 114 is the closest of the three (3) examples to the fluid passageway 148 in the connector port 146. Thus, the radial stress concentration in the connector hub 142 in FIG. 6 is closest to the connector port 146 of the three (3) examples. FIG. 7 shows the end portion 118 with a slightly longer axial length $L_2$ so that the axial position of the tube end 104 within the end element 114 is spaced slightly farther away from the fluid passageway 148 in the connector port 146. Thus, the radial stress concentration in the connector hub 142 in FIG. 7 is now farther away from the connector port 146 of the three (3) examples. FIG. 8 shows the end portion 118 with an even longer axial length $L_2$ so that the axial position of the tube end 104 within the overmolded end element 114 is spaced even farther away from the fluid passageway 148 in the connector port 146 in the three (3) examples present. Thus, the radial stress concentration in the connector hub 142 in FIG. 8 is now the farthest away from the connector port 146 of the three (3) examples. By altering the axial location of the tube end 104 within the overmolded end element 114, which may be accomplished by shortening or lengthening the axial length $L_2$ of the end portion 118 of the tubular body 116 of the end element 114, the stress concentration in the connector hub 142 may be shifted axially along the axial length $L_1$ of the receiving cavity 144 and, hence, along the axial length of the connector hub 142. Thus, the location of stress concentration in the connector hub 142 may be preselected or "pre-controlled" to avoid stress risers at hard interfaces, corners, edges, sharp or prominent surface features, or material thin areas and, alternatively, is preselected or "pre-controlled" to be at specified axial locations along the connector hub 142 desirably having "planar" surface features and generally free of the foregoing stress-inducing features. While the foregoing discussion references connector element 140, the foregoing discussion is equally applicable to connector element 160 or any suitable luer connector element or hub known in the medical field. The present disclosure permits the location of radial stress concentration in a medical connector element to be preselected or "pre-controlled" by adjustments to the axial length of the end portion 118 of the overmolded element 114 on the tube ends 104, 106.

While several embodiments of a high pressure medical connector tubing assembly and components or elements thereof are shown in the accompanying figures and described hereinabove in detail, other embodiments will be apparent to, and readily made by, those skilled in the art without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are to be embraced within their scope.

The invention claimed is:

1. A high pressure medical connector tubing assembly, comprising:
   a tube element comprising opposed tube ends and a passageway therethrough;
   an end element overmolded to at least one of the opposed tube ends to provide an overmolded end element, the end element comprising an annular end portion having a preselected axial length, the annular end portion defining an entranceway; and
   a connector element comprising a connector hub defining a receiving cavity, the tube end with the overmolded end element fixedly secured in the receiving cavity, the connector element comprising a connector port defining a fluid passageway;
   wherein an axial location of radial stress concentration in the connector hub is preselected by changing the axial length of the annular end portion in the receiving cavity; and
   wherein the entranceway and the fluid passageway have a common internal diameter and abut to define a smooth transition seam between the fluid passageway and the entranceway to maintain laminar flow conditions across the smooth transition seam.

2. The high pressure medical connector tubing assembly of claim 1, wherein the tube end with the overmolded end element is fixedly secured in the receiving cavity by solvent bonding.

3. The high pressure medical connector tubing assembly of claim 1, wherein the end element is formed with at least one external indicator to visibly identify depth of insertion of the tube end with the overmolded end element in the receiving cavity.

4. The high pressure medical connector tubing assembly of claim 1, wherein the tube element comprises braided tubing formed of an inner braid encapsulated by a flexible polymer layer.

5. The high pressure medical connector tubing assembly of claim 1, wherein the entranceway tapers downstream of the smooth transition seam to the passageway in the tube element.

6. The high pressure medical connector tubing assembly of claim 5, wherein the entranceway tapers at an angle of approximately between 0° and 80°.

7. The high pressure medical connector tubing assembly of claim 1, wherein an end element is overmolded to each of the opposed tube ends of the tube element.

8. The high pressure medical connector tubing assembly of claim 7, wherein the connector element comprises a pair of connector elements, and the opposed tube ends each having an overmolded end element are fixedly secured, respectively, in the receiving cavities of the pair of connector elements.

9. The high pressure medical connector tubing assembly of claim 7, wherein the tube element comprises braided tubing formed of an inner braid encapsulated by a flexible polymer layer.

10. A method of forming a high pressure medical connector tubing assembly, comprising:
    providing a tube element comprising opposed tube ends and a passageway therethrough;
    overmolding an end element onto at least one of the opposed tube ends to provide an overmolded end element, the end element comprising an annular end portion having a preselected axial length, the annular end portion defining an entranceway;
    providing a connector element comprising a connector hub defining a receiving cavity, the connector element comprising a connector port defining a fluid passageway; and
    securing the tube end with the overmolded end element in the receiving cavity;
    wherein an axial location of radial stress concentration in the connector hub is preselected by changing the axial length of the annular end portion in the receiving cavity; and
    wherein the entranceway and the fluid passageway have a common internal diameter and abut to define a smooth transition seam between the fluid passageway and the entranceway to maintain laminar flow conditions across the smooth transition seam.

11. The method of claim 10, wherein the securing the tube end with the overmolded end element in the receiving cavity comprises solvent bonding the tube end with the overmolded end element in the receiving cavity.

12. The method of claim 10, wherein the end element is formed with at least one external indicator to visibly identify depth of insertion of the tube end with the overmolded end element in the receiving cavity.

13. The method of claim 10, wherein the tube element comprises braided tubing formed of an inner braid encapsulated by a flexible polymer layer.

14. The method of claim 10, wherein the entranceway tapers downstream of the smooth transition seam to the passageway in the tube element.

15. The method of claim 14, wherein the entranceway tapers at an angle of approximately between 0° and 80°.

16. The method of claim 10, further comprising overmolding an end element to each of the opposed tube ends of the tube element.

17. The method of claim 16, wherein the opposed tube ends each having an overmolded end element are fixedly secured, respectively, in the receiving cavities of a pair of connector elements.

18. The method of claim 16, wherein the tube element comprises braided tubing formed of an inner braid encapsulated by a flexible polymer layer.

* * * * *

UNITED STATES PATENT AND TRADEMARK OFFICE
CERTIFICATE OF CORRECTION

PATENT NO. : 9,901,725 B2  
APPLICATION NO. : 13/632598  
DATED : February 27, 2018  
INVENTOR(S) : Spohn et al.

Page 1 of 1

It is certified that error appears in the above-identified patent and that said Letters Patent is hereby corrected as shown below:

In the Specification
In Column 5, Line 44, delete "tube element 120" and insert -- tube element 102 --, therefor.
In Column 5, Line 47, delete "tube element 120." and insert -- tube element 102. --, therefor.

Signed and Sealed this
Seventh Day of August, 2018

Andrei Iancu
*Director of the United States Patent and Trademark Office*